United States Patent [19]

Casile

[11] Patent Number: 4,506,658

[45] Date of Patent: Mar. 26, 1985

[54] PERICARDIAC CIRCULATORY ASSISTANCE DEVICE

[76] Inventor: Jean P. Casile, La Cote d'Hyot, Bonneville (Haute Savoie), France

[21] Appl. No.: 456,343

[22] Filed: Jan. 7, 1983

[30] Foreign Application Priority Data

Jan. 11, 1982 [FR] France ............................. 82 00649

[51] Int. Cl.³ ..................... A61B 19/00; A61F 1/24; A61H 31/00
[52] U.S. Cl. .................... 128/1 D; 128/64; 128/DIG. 3; 3/1.7
[58] Field of Search ............... 128/1 D, DIG. 3, 24.2, 128/24.5, 64; 3/1.7

[56] References Cited

U.S. PATENT DOCUMENTS

| | | | |
|---|---|---|---|
| 3,371,662 | 3/1968 | Heid et al. | 128/24.5 |
| 3,496,932 | 2/1970 | Prisk et al. | 128/64 |
| 3,587,567 | 6/1971 | Schiff | 128/64 X |
| 3,835,845 | 9/1974 | Maher | 128/64 |
| 4,192,293 | 3/1980 | Ascrian | 128/1 D |
| 4,302,854 | 12/1981 | Runge | 3/1.7 |

*Primary Examiner*—Ronald L. Frinks
*Attorney, Agent, or Firm*—Browdy and Neimark

[57] ABSTRACT

A circulatory assistance device for implantation in the human body to assist a failing heart. The device comprises a truncated conical structure, made up of rigid pieces connected by volumetric reduction columns which contain electromechanical means for exerting alternating stress and mechanical means for maintaining the stress. On the inside of the structure are positioned sacs belonging to a double, right and left, hydraulic drive unit comprising pumping means. The truncated conical structure further comprises fastenings for securing the structure in implanted relation in a human body. The structure is connected, by a multiconductor cable to an implantable electric power source and to electronic control means which govern the functioning chronology of the alternating stress and of the double hydraulic drive unit.

12 Claims, 9 Drawing Figures

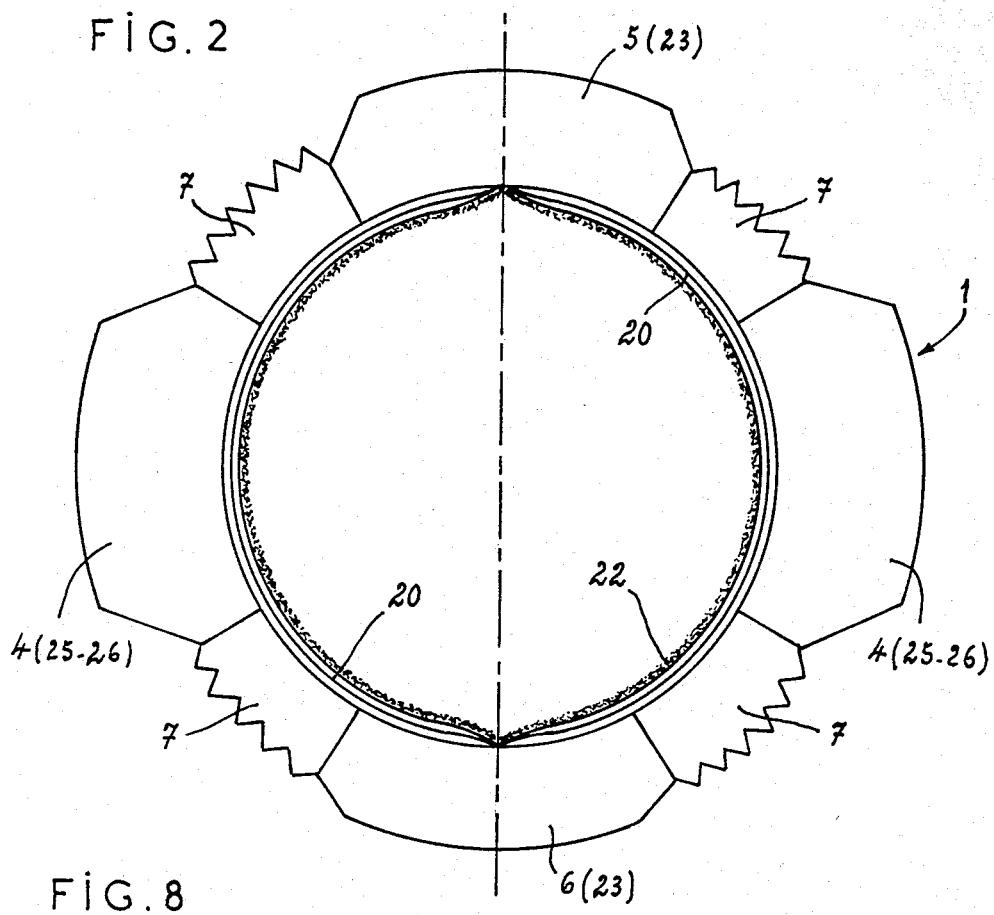
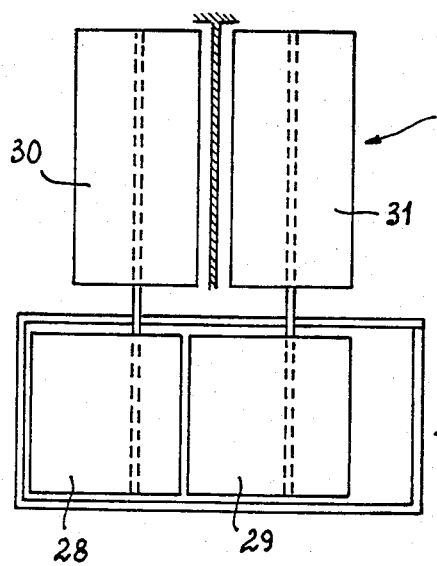
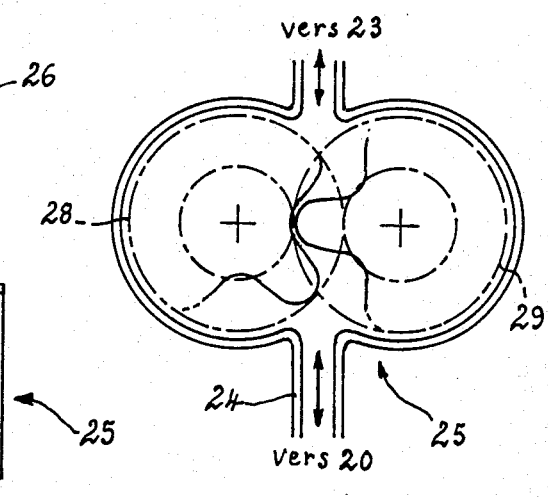

PERICARDIAC CIRCULATORY ASSISTANCE DEVICE

This invention relates to a device for pericardial circulatory assistance; this device, implantable in the human body in intrathoracic position, assists the failing heart in its main blood circulation function, but in the strict sense it is not a prosthesis because it does not replace the failing organ but provides it only an additional effectiveness.

The state of the art, in this field and in related fields, comprises present clinical applications and the systems that have been proposed but do not have known clinical use.

The field of clinical application, besides the medical treatment based on various existing medications, comprised endovascular circulatory assistance systems, of the aortic counterpulsion type which is temporary and not implanted but in aortic intraluminal position.

Systems which have been proposed but are still in the experimental stage comprise the broad category of prosthesis or artificial hearts which are pumps directly assuming the circulatory function, the blood being directly in contact with the device, and whose practical application has especially been hindered by tolerance problems; the blood being a living medium, the complications of such prosthesis are related both to endovascular coagulation and to hemolysis; further, the energy cost of these devices is great, involving a large volume of generators and implantation difficulties.

Perivascular systems at the arterial and not the cardiac stage have also been proposed, which are in a different peripheral position and do not respond to the problem raised here of central circulatory assistance.

French Pat. No. 1,499,305 and its first addition No. 92 798 describe equipment for the purpose of pericardial intracardial circulatory assistance, made up of a flexible double-wall sac, defining "balloons" able to be filled with fluid, as a result of being connected to a pulsation generator. This device does not correspond to an external stress mechanism, the drive unit being free of any stress; fastening is not adequate and the functioning chronology of the hydraulic part, essential to functioning of this system, is not defined in an exact manner.

The present invention remedies these drawbacks and shortcomings by providing a circulatory assistance device placed in intrapericardic pericardial position and supplementing the external working of the failing heart, this device exerting an alternating external stress, respecting the separation of the two circulations, and being provided with a suitable fastening system.

The pericardial circulatory assistance device according to the invention essentially comprises in combination:

- a structure of general truncated conical shape, able to be put in place periventricularly, provided with electromechanical means for applying alternating external stress, and mechanical means for maintaining the stress;
- a double, right and left, hydraulic drive unit, with a sac placed on the inside of said structure and forming part of a circuit comprising pumping means;
- mechanical fastening means provided on the outside of said structure;
- electronic control means governing the functioning chronology of the alternating external stress and the double hydraulic drive unit; and
- an implantable electric power source.

Thus, a first characteristic of the circulatory assistance device, which is the object of the invention, and which is basis for the mechanical efficiency of the device placed pericardially, is its structure which is able to exert an external stress, this stress alternating with respect to the ejection function, called systolic function, and of the filling function, called diastolic function. This structure therefore aims at creating a considerable rigidity during the ejection phase and cancelling it during filling. This cancellation is not only necessary for filling the cardiac pump but also for the safety of the system for the circulation of the blood in the coronary arteries at diastole which is essential for maintaining an underlying myocardial vitality.

The structure, of a general truncated conical shape as already indicated hereinbefore advantageously consists of an even number of rigid pieces constituting the parts having truncated conical surfaces, joined to one another by means making possible translation movements corresponding to the approach or separation of two consecutive rigid pieces, and also joined by volumetric reduction columns, which are extensible and retractable in the circumferential direction of the structure considered, which contain electromechanical means for exerting alternating stress and mechanical means for maintaining the stress.

Preferably, there are provided four rigid pieces and four reduction columns, which are equidistant, symmetrical in pairs in relation to the cardiac septal plane. The choice of this number of columns and their location results from a concern for safety, because of the risk of adiastole, i.e., impossibility of filling, linked to poor functioning of columns in an insufficient number and because of the anatomic arrangement of the coronary arterial network.

The electromechanical means for applying alternating stress preferably comprise, for each reduction column, at least two electromagnets with a plunger core acting in the circumferential direction so as to move two consecutive truncated conical rigid pieces of the structure under consideration toward or away from one another. The means for maintaining the stress comprise, for each reduction column, at least a hook connected to one of the truncated conical pieces and cooperating with a mechanical locking element connected to the other truncated conical rigid piece and able to move in the direction of a generatrix against the action of a recall spring under the control of an electromagnet.

After an active volumetric reduction by the action of the first electromagnet acting in a circumferential direction, a mechanical locking of the unit of the truncated conical structure is made by a simultaneous hooking of the four rigid pieces, caused by other electromagnets but being maintained without input of electric power. Thus, during the systole, a rigid unit is obtained that makes possible a maximum energy output for the double hydraulic drive unit, whose makeup will be specified hereinafter. Cancellation of the locking at the end of systole allows the passive free expansion of the external stress system during filling of the cardiac cavities; if it should prove necessary, it can easily be made active by electromagnetic elements like those described hereinbefore, although this is not necessary if the extrinsic freedom of the stress system is respected (wide pericardotomy or pericardectomy associated with implantation of the device).

The electromagnetic nature of the means that intervene to initiate or cancel the stress permits their electronic control, the latter governing the functioning chronology, a basic idea for both the hemodynamic efficiency of the system and its safety.

Finally, the excellent energy efficiency of the stress system should be emphasized since only activation of the electromagnetic elements consumes energy, which is extremely short and relates to minimal forces.

The fastening means, essential for application of the stress, add a relative immobility of the device to the perisystolic rigidity of the stress system. These means, assuring anchoring to the existing anatomic structures, logically are inspired by a pericardial anatomy and should also meet the criteria of safety for the coronary network, the auricular myocardium and the neighboring mediastinal organs. For this purpose, the invention proposes a fourfold fastening, with:

- an upper fastening for pre- and peri-aortic attachment, fastened to the rigid piece of the truncated conical structure with front arrangement;
- a lower fastening for phrenic attachment, symmetrical with the preceding one inserted in the rigid piece of the truncated conical structure with lower arrangement;
- a back fastening with prevertebral attachment, designed as an expansion of the lower fastening; and
- a front fastening for retrosternal attachment, designed as an expansion of the multiconductor cable for power supply and electronic control ending at the top of the truncated conical structure.

This fastening system keeping the front and back rigid pieces of said structure immobile, the expansion, during filling, will preferably be performed laterally.

The double hydraulic drive unit consists for each elementary unit, right and left, of at least a sac fastened on the inside of the truncated conical structure, exerting the alternating external stress and connected to a buffer volume, carried by said structure, by a duct in which a pump is inserted, the unit constituting a closed circuit filled with fluid. The two (right and left) elementary units are symmetrical in relation to the nonsagittal and cardiac septal plane; the functioning of these units as simultaneous, only the internal pressure operating conditions differing, in proportion to the difference existing between the two, systemic and pulmonary, circulations. For safety, it is possible to consider doubling the hydraulic system to prevent nonfunctioning of a pump, by then providing, for each elementary unit, two concentric sacs, connected respectively to two buffer volumes by two similar pumps, both circuits being closed and separate.

Preferably, the sacs of the two, right and left, units, are fastened lengthwise to the two volumetric reduction columns of the truncated conical structure, to achieve a partial inclusion of each sac in the corresponding column during contraction of this column, so that it does not constitute a stress at filling, or in the opposite case of redundancy, an element running the risk of injuring the underlying cardiac structures during the ejection phase. Further, each sac remains free on its outside edge of any attachment with the other sac belonging to the other unit, and the inside coating which will be contiguous with the myocardium will advantageously be reinforced with a protective layer, particularly of foam plastic.

The pumps and their motors, according to a possible configuration, will be placed in the rigid pieces of the truncated conical structure with lateral arrangement, because of greater size than that of the buffer volumes which, in this case, will be placed respectively in the two rigid pieces with front and back arrangement. Because of their size and noise, the pumps will preferably be gear or or vane type pumps, which have the further advantage of functioning without valves, cams or eccentrics, in a closed circuit and equally in both directions, by alternately using the two gear shafts as driving shafts, thus making possible not only an active inflation but also emptying of the sacs.

The volume displaced by each unit, whether it is divided in two or not, should be greater than the volume of desired systolic ejection, by about 30%, given the inevitably imperfect congruence between the internal surface of the sacs and myocardium. The delivery capacity should be provided to move about 50 or 100 cc, depending on the duplication or not of the sacs and hydraulic circuits on each, right and left, side and in 200 ms, on the average, depending on the options chosen for the functioning chronology; the admissible pressures used are on the order of 150 mmHg on the right and 300 mmHg on the left, while for physical functioning reasons they are rarely attained but safety requires putting manometric reduction valves in place. For a motor running at a constant speed and a pump with a presumably correct delivery, the pressure will be established as a function of the resistances encountered, therefore equally in the two, right and left, units, and will be slight until congruence of the hydraulic systems is obtained, then with progressively increasing rise as a function of the combined resistance of the vascular resistances and the ventricular parietal mechanical resistance, until a maximum at the end of systole, the drop in pressure then occurring by removal of the stress and preferably active emptying of the internal hydraulic unit, with an emptying motor if needed. Therefore, the aforementioned manometric reduction valves will come into play before the start of active emptying only in case of malfunctioning of the system or of very high vascular or parietal resistances.

In any case, the invention will be better understood from the following description, with reference to the accompanying diagrammatic drawing representing, by way of nonlimiting example, an embodiment of this pericardial circulatory assistance device:

FIG. 2 is a view in cross section of the device of FIG. 1 taken in a plane perpendicular to its main axis;

Figure 3:
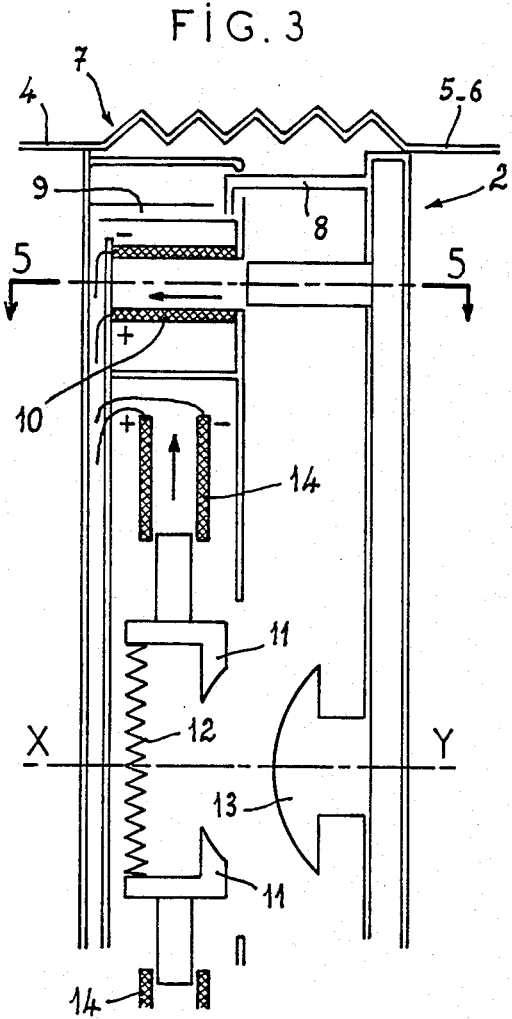
FIGS. 3 and 4 are partial views, in lengthwise section, of one of the volumetric reduction columns, in open position and closed position, respectively.
Figure 4:
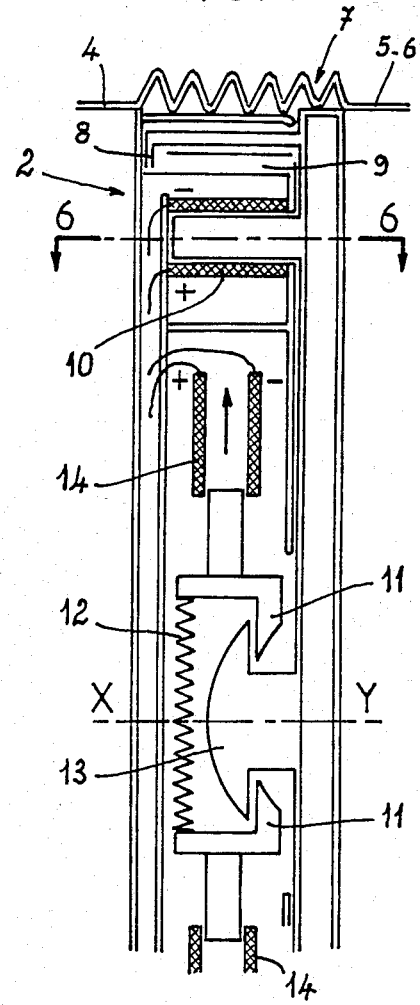
Figure 5:
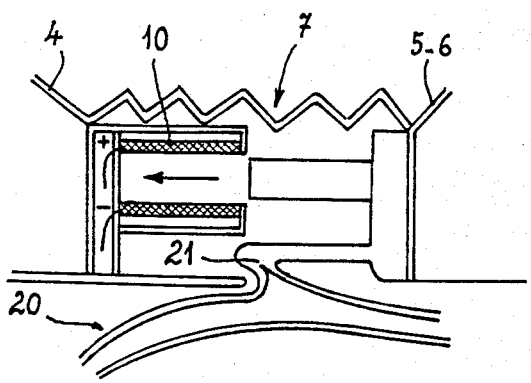
Figure 6:
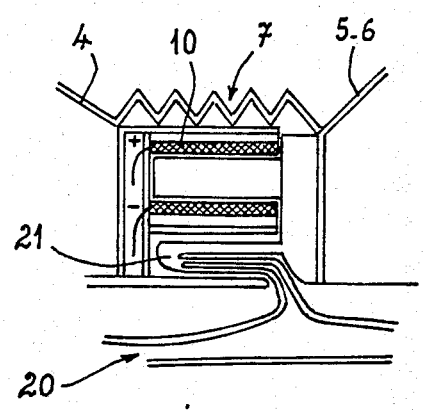
Figure 7:
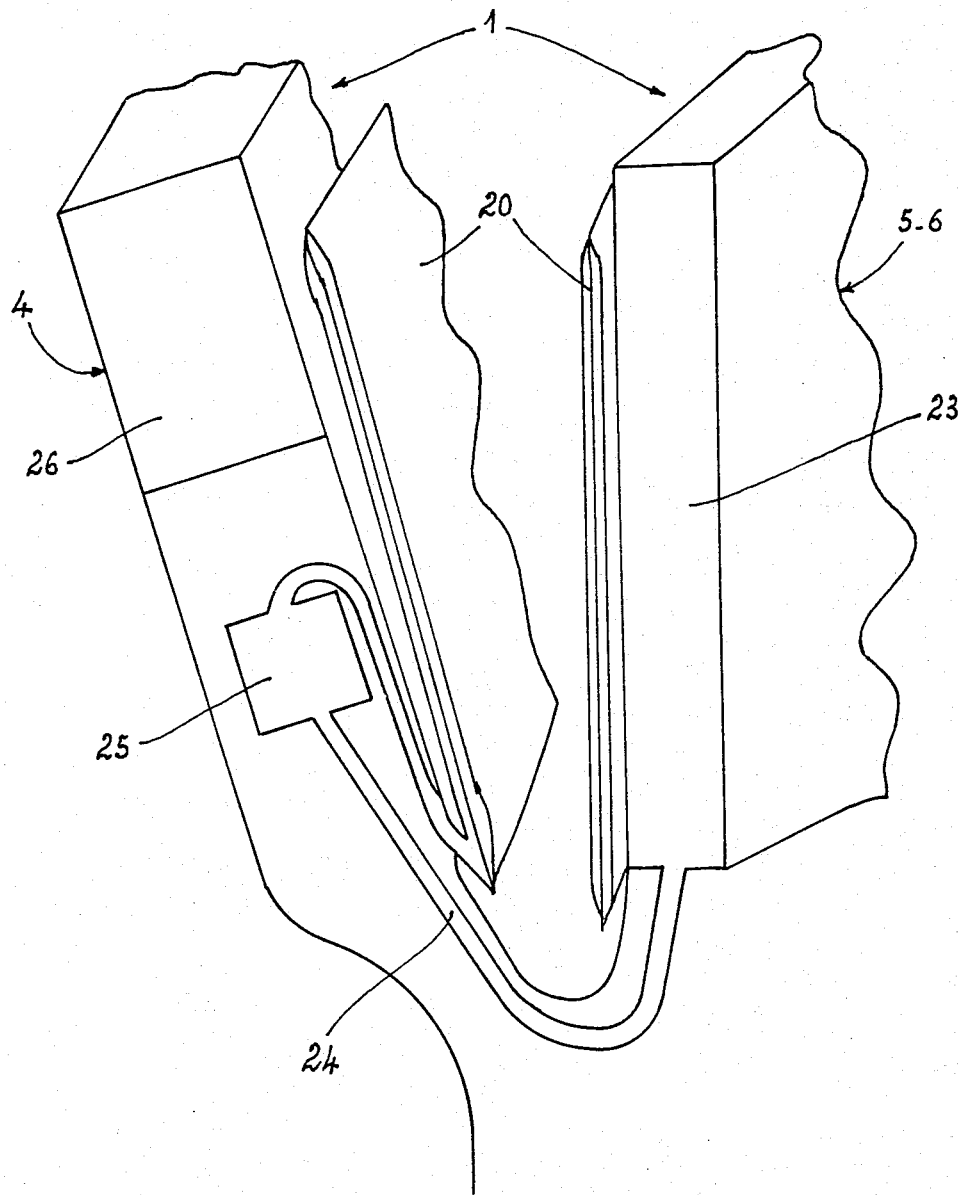

FIGS. 5 and 6 are views in cross section along section line 5—5 of FIG. 3 and along section line 6—6 of FIG. 4, respectively;

FIG. 7 is a partial view, in perspective and with sections, showing the makeup of an elementary hydraulic drive unit; and FIGS. 8 and 9 are diagrammatic views representing, in lengthwise view and in transverse cross section, a gear type pump that can be used in each elementary hydraulic drive unit.

Figure 1:
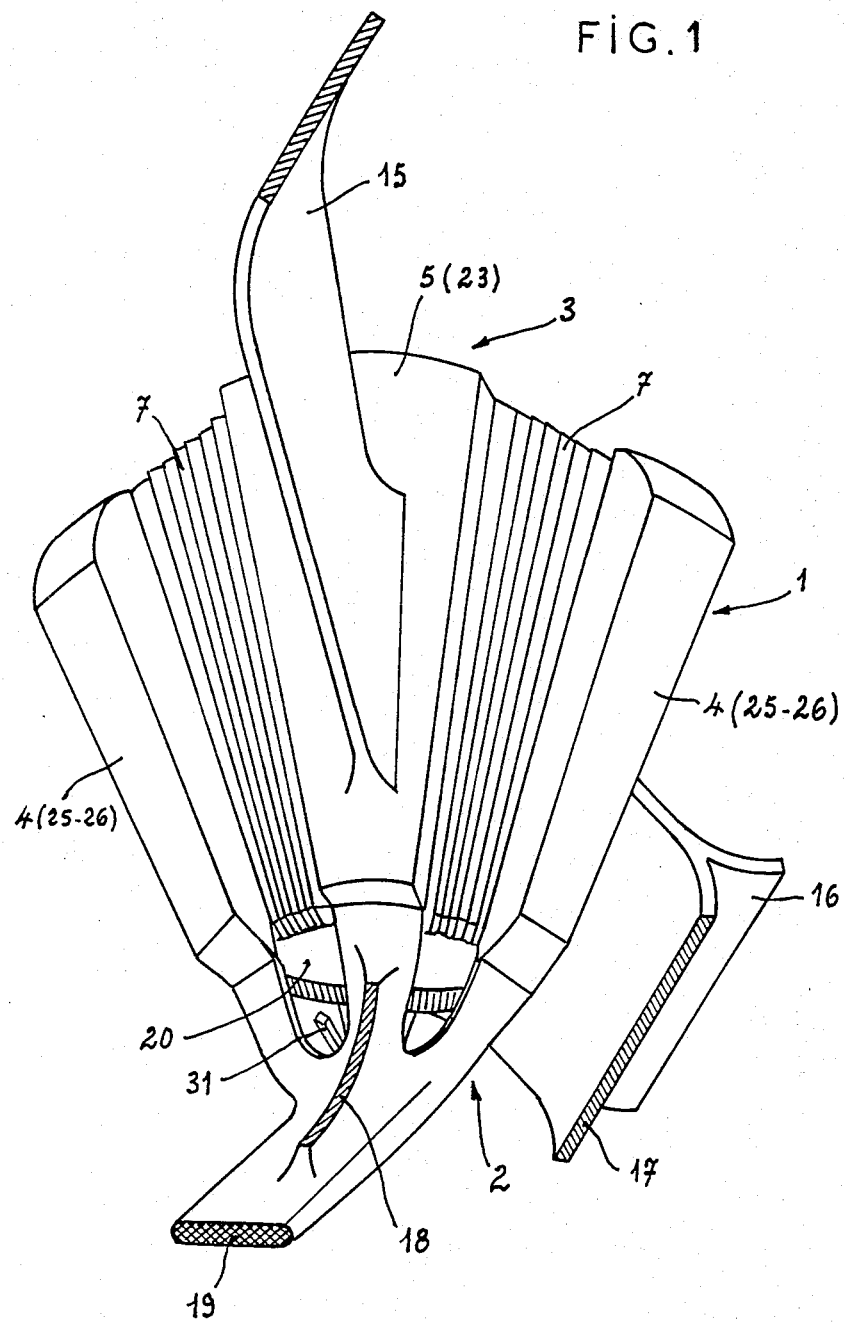
FIG. 1 is an overall view, in perspective, of a circulatory assistance device according to the invention, with leads of its power supply cable and its various fastenings.

The device as best seen in FIGS. 1 and 2 comprised a structure of a generally truncated conical shape, designated in its entirety by 1, constituting a system of alternating external stress. This truncated conical structure 1 is intended to be put in place periventricularly, with the extreme cardiac tip being at the level of summit 2 of structure 1 and the largest part of the auricular surface being at the level of base 3 of structure 1.

Truncated conical structure 1 comprises four rigid pieces constituting the parts of the truncated conical surfaces, called lateral piece 4, front piece 5 and lower piece 6, that can be made of an inextensible plastic, known for its toxicological and immunological harmlessness in regard to the human organism. The four rigid pieces 4, 5, 6 are separated from one another by four deformable parts 7 called volumetric reduction columns, externally having a bellows appearance, each reduction column 7 connecting two consecutive rigid pieces, along their entire height. As FIGS. 3 and 4 show, two consecutive rigid pieces, such as 4 and 5 or 4 and 6, are joined to one another, at summit 2 and at the base of the device (XY designating a plane of symmetry), by insertion of hooks 8 secured to piece 5 or 6 in slide guides 9 secured to piece 4.

In each reduction column 7 are placed two armored electromagnets 10, with a plunger core, one located near summit 2 and the other, not shown, near the base in symmetrical position with the first in relation to plane XY. Electromagnets 10 act in the circumferential direction and allow passage from open position, shown in FIGS. 3 and 5 (corresponding to the filling phase) to the closed position, shown in FIGS. 4 and 6 (corresponding to the ejection phase).

In this latter position, the stress is maintained by the action of two mechanical locking elements 11, which are connected, for example, to rigid piece 4 and which, brought together by a recall spring 12, are locked on both sides of a double hook 13 connected to rigid piece 5 or 6. Each locking element 11 can move, in the direction of a generatrix and against the action of recall spring 12, under the control of another armored electromagnet 14, with a plunger core, also housed in reduction column 7.

The fastenings of the device, partially represented in FIG. 1, comprise:
  an upper fastening 15 for pre- and peri-aortic attachment, inserted in front rigid piece 5;
  a lower fastening 16 for phrenic attachment, inserted symmetrically with the preceding one in lower rigid piece 6;
  a back fastening 15 for prevertebral attachment, made as an expansion of lower fastening 16; and
  a front fastening 18 for retrosternal attachment, made as an expansion of the multiconductor cable 19 which connects the electronic control and electric power batteries, placed on the outside, to the device properly so-called.

On the inside of truncated conical structure 1 are placed, as FIGS. 2 and 7 show, two sacs 20 each of which is fastened longitudinally to a volumetric reduction column 7 by fastener 21 made to obtain a partial inclusion of this sac 20 in column 7 during contraction of this latter (compare FIGS. 5 and 6). Each sac 20 has an inside lining contiguous with the myocardium, reinforced with a layer of protective foam plastic 22.

As FIG. 7 shows, each sac 20 is connected to a buffer volume 23, housed in front rigid piece 5 or lower rigid piece 6, by a duct 24 in which is inserted a pump 25 driven by a motor unit 26, pump 25 and its motor unit 26 being housed in one of the two lateral rigid pieces 4.

The elementary drive units, each with a closed circuit filled with a fluid, are thus constituted.

Pump 25 and its motor unit 26 can particularly consist, as FIGS. 8 and 9 show, of a gear pump, with two pinions 28 and 29 meshed respectively with two small electric motors 30 and 31, functioning alternately and in opposite directions, one for filling and the other for expulsion.

The entire circulatory assistance device described so far is connected, by a multicoupler cable 19, to an electronic control system, having the function of chronological distribution of the task between the various constituent elements of the device. This control system is not shown, except by the epicardial electrodes 31 that can be seen in FIG. 1, and its electronic components will not be detailed; they are known, for the most part, as pacemakers now widely used for cardiac electrosystolic driving.

The control system will, first of all, be provided with a monitoring function which will analyze the occurrence of electromotive forces of ventricular depolarization of the patient, similar to that of pacemakers, a depolarization that will mark the start of the periods of the functioning cycle of the device.

The period of myocardial inexcitability starts at the original period thus defined; it ends at the vulnerable period which marks the end of ventricular repolarization. This period constitutes the active period of the device during which the rhythmic harmlessness given by the inexcitabieity of the myocardium allows activation of the external stress and hydraulic drive unit. On the other hand, functioning of the device should not transmit to the myocardium mechanical excitation of any kind, outside this period. Thus, cancellation of the external stress that occurs after active emptying of the hydraulic unit should never be simultaneous with or later than the so-called vulnerable period.

Starting from this general principle of the functioning of the control system as far as chronology is concerned, all modalities and all improvements in regard to various rhythmological situations, in which the device will be used, can be conceived.

As a starting concept, activation of the mechanical stress should follow the end of ventricular depolarization, identified by the monitoring function, of a fixed period, for example, 20 to 31 milleseconds; also a fixed period on the same order, or even shorter, should separate the mechanical stress from activation of the hydraulic drive unit, which can be simultaneous or successive inside of each right and left, of the elementary units. Activation Simultaneous is better if it is desired that the duality provide assistance in case of malfunctioning, but in any case, necessarily simultaneous in regard to the two, right and left, subunits, whether or not these units are divided into two.

Interruption of the assistance provided by the hydraulic unit and its active emptying, which immediately follows it, should be separated from electromechanical cancellation of the external stress by a short, fixed period, ending the active period of the device, which then goes into the passive filling phase.

It remains to define the chronology of the interruption of the assistance in relation to its activation, the hydraulic effectiveness period, which should be sufficient to be effective but not traumatizing, but such that the whole functioning described above does not exceed the inexcitability period. It can also be fixed, for example 150 ms, or a total active period on the order of 220 ms, permitting high frequencies, knowing not only the occurrence of the last depolarization but also the period separating the last two depolarizations, an evaluation made in present sentinel pacemakers, it seems more logical that the period of the assistance function should be variable, in discontinuous function admitting only two or three values; even in this hypothesis, the other period defined hereinbefore remain fixed, their variability not having any practical advantage.

The electronic control system should finally be able to impose the cardiac rhythm or the hemodynamic functioning in case of a major rhythmic incident or acute circulatory deficiency.

Thus, the device is preferably equipped with a demand pacemaker to oppose cardiac arrest, the control system functioning normally on the data of ventricular depolarization induced by electrosystolic drive of the demand pacemaker with unipolar electrode sutured to the apex of the heart, but this is not obligatory, a precordial pacemaker implanted endovenously being able to perform the same service.

The second emergency situation the device has to be able to meet is ventricular fibrillation which the data electrode should detect, which in two cases—high frequency succession of depolarization data or the absence thereof—will bring into play a constant frequency functioning of the external stress and and the hydraulic drive unit, a functioning that will be cancelled by finding of a suitable depolarization periodicity.

The physical position of the control system is preferably extrathoracic, because the mobility of the mechanical elements is not a priori compatible with the long life of the electronic equipment. On the other hand, it is necessary that there be a close connection with the electric generators, and it is good to be able to have easy access to this electronic control system, given the immediate prognostic importance that a possible malfunction of the system would cause.

The electric power source, to which the device resorts for energy supply to electromagnets 10 and 14 and motor units 26, will advantageously consist of lithium batteries, which are satisfactory from the viewpoint of long life, weight and bulk. On the plane of the energy balance, activating and deactivating the stress bring minimal forces into play for very short periods, so that the electromagnets will consume little energy and the main energy demand will come from the hydraulic drive units. However, this energy demand should not be considerable for a beating heart, with synchronization of the functioning of the device described hereinbefore. Actually, the work provided will be equal to the difference between the external work of the assisted heart and the external work of the failing heart, which should be improved precisely by the assistance which will put the myocardium of the patient in better hemodynamic, particularly filling, conditions.

In practice, the electronic control system and the batteries will be put in a single unit, implantable on the patient in extrathoracic position. This unit will be connected to the assistance device of the invention, by multiconductor cable 19, whose expansion serves as a fastener 18 to structure 1 as already described, and whose other expansion is sutured to the apex of the heart with two electrodes 31, one of unipolar stimulation connected to a pacemaker having only a role of demand electrosystolic drive, the other having the role of collecting information necessary for the monitoring function of the control system. The device can be considered for the extreme cardiac tip, as already indicated above, not only for reasons of prophylaxis for embolic accidents but also for the insertion of double electrode 31. Multiconductor cable 19 contains both the incoming conductors to the control system necessary for collection of data on ventricular depolarization and the outgoing conductors intended for ventricular stimulation and to each electromechanical unit of the stress system and to each pump of the hydraulic drive unit.

It goes without saying that the invention is not limited to the sole embodiment of this pericardial circulatory assistance device which was described hereinbefore by way of example; on the contrary, it encompasses all variants based on the same principle, and can differ from the example described by resorting to equivalent means or addition of complementary systems.

I claim:

1. A pericardial circulatory assistance device, comprising in combination:
   a structure of generally truncated conical shape adapted to be positioned periventricularly in the human body, said structure being provided with electromechanical means for exerting alternating external stress, and mechanical means for maintaining the stress;
   a double, right and left, hydraulic drive unit positioned inside said structure, each of the right and left of said double hydraulic drive unit being in hydraulic circuit with a corresponding fluid-receiving sac positioned inside said structure, said double, right and left, hydraulic drive unit and the corresponding fluid-receiving sacs being in a closed circuit comprising pumping means mechanical fastening means carried by said structure for securing said structure in implanted relation to the human body;
   electronic control means governing the functioning chronology of the alternating external stress and of said double hydraulic drive unit; and
   an implantable electric power source for said device.

2. A pericardial circulatory assistance device as defined in claim 1, wherein said truncated conical structure comprises an even number of rigid pieces constituting parts having truncated conical surfaces, said rigid pieces being joined to one another by means permitting translation movements corresponding to the approach or withdrawal of two consecutive rigid pieces; said rigid pieces also being connected by volumetric reduction columns that are extensible and retractable in the circumferential direction of said structure, said volumetric reduction columns containing said electromechanical means for exerting alternating stress and also containing mechanical means for maintaining the stress.

3. A pericardial circulatory assistance device as in claim 2, wherein said truncated conical structure comprises four rigid pieces and four volumetric reduction columns symmetrical in pairs in relation to the cardiac septal plane.

4. A pericardial circulatory assistance device as in claim 2 or 3, wherein said electromechanical means for exerting alternating stress comprises, for each reduction column, at least two electromagnets respectively having a plunger core acting in the circumferential direction, to bring together or to separate two consecutive rigid pieces of the structure, while the means for maintaining the stress comprise, for each reduction column at least a hook connected to one of the truncated conical rigid pieces and cooperating with a mechanical locking element connected to the other truncated conical rigid piece and able to move along a generatrix against the action of a recall spring under the control of an additional electromagnet.

5. A pericardial circulatory assistance device as in claim 3, wherein said fastening means comprises:
- an upper fastening for pre- and peri-aortic attachment, inserted in the rigid piece of the truncated conical structure with front arrangement;
- a lower fastening for phrenic attachment, symmetrical with the preceding one, inserted in the rigid piece of the truncated conical structure with lower arrangement;
- a back fastening for prevertebral attachment, designed as an expansion of said lower fastening; and
- a front fastening for retrosternal attachment, designed as an expansion of the multiconductor cable for power supply and electronic control ending at the top of the truncated conical structure.

6. A pericardial circulatory assistance device as defined in claim 1 wherein said double hydraulic drive unit consists, in regard to each, right or left, elementary unit, of at least a sac fastened on the inside of said truncated conical structure, said sac being connected to a buffer volume, carried by said structure, by a duct in circuit with a pump, said unit constituting a closed circuit filled with fluid.

7. A pericardial circulatory assistance device as defined in claim 6, wherein said hydraulic system is doubled, each elementary unit comprising two concentric sacs, connected respectively to two buffer volumes by two similar pumps, the two circuits being closed and separated.

8. A pericardial circulatory assistance device as defined in claim 2 or 7, wherein said sacs of the two elementary hydraulic drive units are fastened lengthwise on two volumetric reduction columns of the truncated conical structure to achieve a partial inclusion of each sac in the corresponding column during contraction of this column.

9. A pericardial circulatory assistance device as defined in claim 6 wherein the internal lining of each sac is reinforced by a protective layer, particularly of foam plastic.

10. A pericardial circulatory assistance device as in claim 3 or 6, wherein the pumps of the two elementary hydraulic drive units and their motors are placed in the two rigid pieces of the truncated conical structure with lateral arrangement, while the buffer volumes are respectively placed in the two rigid pieces with front and back arrangement.

11. A pericardial circulatory assistance device as defined in claim 6, wherein the pumps of the double hydraulic drive unit are of the gear type, with two pinions meshed respectively with two electric motors functioning alternately and in opposite directions.

12. A pericardial circulatory assistance device as defined in claim 1 having associated therewith a pacemaker and comprising, at the top of the truncated conical structure a double electrode for stimulation, connected to said pacemaker, and for collection of data necessary for the monitoring function of the control system of said device.

* * * * *